United States Patent [19]

Weiner et al.

[11] 4,397,846

[45] Aug. 9, 1983

[54] STORAGE-STABLE LIPID VESICLES AND METHOD OF PREPARATION

[76] Inventors: Murray Weiner, 8915 Spooky Ridge La., Cincinnati, Ohio 45242; Klaus Gersonde, Preusweg 69, D-5100 Aachen, Fed. Rep. of Germany

[21] Appl. No.: 263,942

[22] Filed: May 15, 1981

[51] Int. Cl.³ .................... A61K 31/685; A61K 45/00
[52] U.S. Cl. ...................................... 424/199; 424/365
[58] Field of Search ................................ 424/199, 365

[56] References Cited

U.S. PATENT DOCUMENTS 4,311,712  1/1982  Evans et al. ......................... 424/365

Primary Examiner—Sam Rosen
Attorney, Agent, or Firm—Ernest F. Marmorek

[57] ABSTRACT

Lipid vesicles, such as those containing inositol hexaphosphate useful for improving the oxygen-release of intact erythrocytes, may be rendered stable to long term storage at temperatures below the freezing point of the encapsulated solution, by rapid freezing at a temperature of from about −196° C. to about −30° C.

12 Claims, 2 Drawing Figures

STORAGE-STABLE LIPID VESICLES AND METHOD OF PREPARATION

BACKGROUND OF THE INVENTION

In recent years much attention has been focused upon the discovery that biologically active substances can be carried into living cells through the mediation of tiny lipid vesicles, also known as liposomes. Such lipid vesicles comprise monolamellar phospholipid membranes encapsulating aqueous solutions of the biologically active substances and are provided as suspensions in aqueous carriers. The progress of lipid vesicle therapy from the research laboratory to practical medical application has been slow, however, as lipid vesicles are not storage stable and must be prepared immediately before use in order to be fully effective.

A constant supply of dioxygen is required by tissues for the maintenance of metabolism. Many medical situations involve an immediate or prolonged deficiency in the oxygen supply to the tissues, for example, in cardiovascular failure, shock due to blood loss, atherosclerosis and other occlusive vascular disease, erythrocyte enzyme defects, hemolytic anemia, and defects in blood oxygenation due to low oxygen pressure or lung disease. Increase in the supply of oxygen to the red blood cells by administration of gaseous oxygen may have little influence on the amount of oxygen delivered to some tissues. The relatively high oxygen affinity of hemoglobin in red blood cells stored in blood banks and in vivo under certain adverse conditions can result in the release of only a small and inadequate fraction of the hemoglobin-bound oxygen to some critical tissues during circulation.

The normally high oxygen affinity of hemoglobin is reduced in the presence of certain chemical substances known as allosteric effectors, some of which are important natural components of red cells. One of the most potent of these effectors is inositol hexaphosphate, IHP. The incorporation of IHP into intact erythrocytes may be accomplished by incubating the erythrocytes with lipid vesicles containing IHP in a phospholipid membrane, according to the method disclosed by Y-C. Nicolau and K. Gersonde in U.S. Pat. No. 4,192,869, whereby the lipid membrane fuses with erythrocyte cell membrane and the IHP is incorporated into the cell. Upon their return to the circulating blood the IHP-containing erythrocytes release to the tissues a larger fraction of the oxygen they absorbed in the lungs, resulting in increases in the total amount of oxygen supplied to the tissues and allowing a higher tissue oxygen pressure. The reduced oxygen affinity of the hemoglobin contained in the modified erythrocytes is retained for the life of the red cell.

Lipid vesicles laden with IHP begin to lose their ability to cause inositol hexaphosphate to penetrate the erythrocyte membrane within a few hours if they are stored at temperatures above their phase transition temperature. Storage at 37° C. (this temperature is not only the temperature of the physiological environment of the red blood cells but is also higher than the phase transition temperature which is necessary to enhance the fusion of vesicles with the cell membrane) leads to a mutual fusion of the lipid vesicles. This fusion leads to the formation of large multilamellar vesicles which cannot transport the IHP into red cells and thereby decrease their oxygen affinity. FIG. 1 demonstrates the half-life of unilamellar lipid vesicles at 37° C. This half-life time depends on the differences in phospholipid composition. The vesicle-mediated IHP uptake is measured as change in the $O_2$ half-saturation pressure, of the red blood cells under standard conditions (see also Y. C. Nicolau and K. Gersonde in U.S. Pat. No. 4,192,869).

Until now lipid vesicles could not be stored longer than one to two days and had to be produced anew each time their use was required. The need for the energy- and frequency-controlled sonication procedure at the time and place wherein the modification of the erythrocytes or the administration of lipid vesicle-encapsulated drugs is to be performed limits the usefulness of this procedure and of other medical procedures employing liposome mediated administration of drugs.

The study and potential clinical use of IHP modified erythrocytes is thus severely handicapped by the instability of the lipid vesicles which make it necessary to prepare the IHP-containing lipid vesicles within hours of their use, limiting their use to locations where apparatus is available for preparing the lipid vesicles and increasing the time required for the process of modifying erythrocytes to treat patients. Lipid vesicle suspensions for modifying erythrocytes of patients have to be produced under absolutely sterile conditions. Furthermore, the lipids and the lipid vesicles have to be produced and stored under anaerobic conditions to avoid oxidation of phospholipids and a loss of effectivity to mediate IHP incorporation by cells. These processes therefore have to be performed under servere control, which is possible only in special laboratories. The constraints of lipid membrane instability to heat and oxidation equally limit the usefulness of lipid vesicles laden with biologically active substances other than IHP. The present invention overcomes this problem.

SUMMARY OF THE INVENTION

The present invention encompasses a process for rendering storage-stable suspensions of lipid vesicles containing biologically active agents, especially those containing allosteric effectors, and the storage-stable lipid vesicles so prepared.

It has now been discovered that lipid vesicles such as those prepared according to the method of U.S. Pat. No. 4,192,869, may be rendered storage-stable by freezing at a temperature of from about $-196°$ to about $-30°$ C. Surprisingly, deep-frozen effector-laden lipid vesicles have been found to remain intact and unfragmented following freezing and thawing and to retain their capacity to fuse with erythrocytes and to facilitate IHP uptake by the red cells.

Inositol hexaphosphate incorporation into erythrocytes has, in fact, been found to be improved when previously frozen lipid vesicle suspensions are employed instead of freshly prepared lipid vesicles.

Frozen lipid vesicle suspensions are stable at freezer temperatures for prolonged periods. They may be prepared at a central location and shipped in the frozen state to hospitals and blood banks where they can be kept frozen and available for immediate use by thawing and dilution when needed.

BRIEF DESCRIPTION OF THE DRAWINGS

In the accompanying drawings

DETAILED DESCRIPTION OF THE INVENTION

Figure 1:
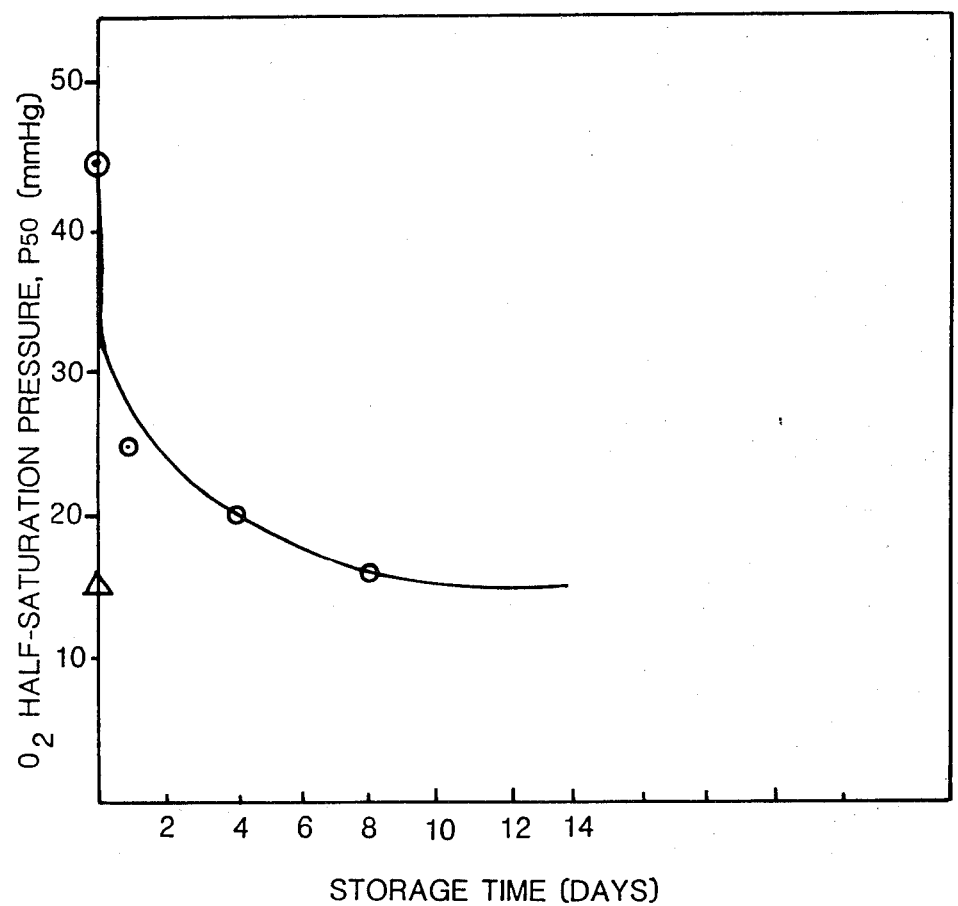
FIG. 1 is a graph showing the IHP uptake by RBC measured as change in $p_{50}$ medicated by V2 vesicles with 0.19 M IHP in the inside and in the outside medium respectively, stored at 37° C. ( O O O ); Δ represents fresh RBC before incubation with V2 vesicles.

IHP uptake by RBC measured as change in $p_{50}$ mediated by V2 vesicles as discussed hereinbefore, is shown in FIG. 1. By selecting an appropriate biologically active agent, an appropriate lipid composition, and an appropriate route of administration, it is possible to treat targeted tissues or organs selectively with lipid vesicle-encapsulated agents. Agents which may be administered by means of lipid vesicles include antitumor agents, antibiotics, antiprotozoals, metal chelating agents, hormones, enzymes, and allosteric effectors. Lipids suitable for the preparation of vesicle membranes include phospholipids, such as phosphatidylcholine, phosphatidylserine and sphingomyelin, glycolipids, such as phosphatidylinositol, charged lipids, such as diacetylphosphate and octadecylamine, steroids, such as cholesterol, and mixtures thereof. Lipid vesicle suspensions may be prepared and the route and site of administration selected so as to ensure that the encapsulated drug is targeted to the cells wherein the therapeutic effect is required. For example a suitably formulated liposome suspension may be administered intravenously in order that the lipid vesicles be carried to the liver, spleen or lungs; intramuscularly, in order that the lipid vesicles be concentrated in the surrounding lymph nodes; or orally, in order that the encapsulated drug be released in a selected portion of the gut. Lipid vesicle suspensions may also be incubated in vitro with living blood cells and the biologically active agent thereby incorporated into the cells, which are then transfused to a patient. Such modified blood cells may act as circulating sustained release carriers for the incorporated agent or may be modified so as to change the properties of the blood cell itself; for example the oxygen release properties of the erythrocyte may be modified by incorporation of an allosteric effector, such as inositol hexaphosphate.

Erythrocytes having incorporated an allosteric effector, such as IHP, and which therefore provide an improved $O_2$ supply to the tissues, may find their use in the following cases:

Circulatory deficiencies
  General (shock)
  Specific
    cerebral, myocardial, peripheral, acute and chronic
Pulmonary deficiencies
  Deficient blood oxygenation
  Hamatopoietin-mediated disturbances
    (secondary polycythemia)
Chronic anemias
  Functional capacity at low hemoglobin levels
  Reduced iron retention from repeated transfusions
  Help control consequences of abnormal hemoglobins
Other
  Alter cancer/normal tissue ratio of sensitivity to radiation, alkylators, etc.
  Effect on carbon monoxide exposure
  "Rejuvenate" outdated blood
  Enhance efficacy of antithrombotic hemodilution by enhancing $O_2$ delivery of low hematocrit blood
  Consequences of left-shifted diabetic Hb $A_{1C}$ The preferred allosteric effector is inositol hexaphosphate. The modification of erythrocytes according to the present invention may employ other allosteric effectors having a larger affinity to hemoglobin than the physiologic effectors, 2,3-bisphosphoglycerate and adenosine triphosphate. Other polyphosphates such as inositol pentaphosphate and inositol tetraphosphate may be suitable, especially for the modification of erythrocytes of species of animals other than humans. In case of certain mutations of hemoglobin, e.g., "Zurich" hemoglobin, organic anions, as polycarboxylic acids, can be used as allosteric effectors.

Lipid vesicles comprising mixtures of phosphatidylcholine, phosphatidylserine and cholesterol in a molar ratio of 10 to 5:4 to 1:10 to 3 are suitable as carriers for the irreversible incorporation of such allosteric effectors into erythrocytes. The method for preparing the lipid vesicles and for their use in preparing erythrocytes having modified oxygen affinity are described in U.S. Pat. No. 4,192,869, which is hereby incorporated by reference.

Phosphatidylcholine, phosphatidylserine and cholesterol are readily commercially available, as is inositol hexaphosphate. The preferred lipid composition comprises phosphatidylcholine, phosphatidylserine and cholesterol in a molar ratio of 8:2:7.

The general methods for preparing lipid vesicles are well known. The lipids are dissolved in an organic solvent to form a uniform solution, from which the organic solvent is removed by evaporation. The resulting lipid film is then agitated with an aqueous solution of the biologically active substance, such as an allosteric effector, preferably by energy and frequency controlled sonication, to form closed sacs enclosing droplets of the aqueous solution. Preferably, for the intended purpose, the lipid mixture is sonicated in a buffered, saturated or near saturated inositol hexaphosphate solution of pH 7.0–8.0. The lipid may be present at a concentration of from about 17 μg/ml. to about 200 μg/ml. of solution. After sonication at an energy above 100 W/cm$^2$, the product is a suspension of unilamellar lipid vesicles of diameter ≦500 A in which is encapsulated the buffered, saturated, aqueous IHP solution. The resulting suspension may be diluted with water, buffer, or additional IHP solution prior to incubation with the erythrocytes. The concentration of salts in the solution surrounding the lipid vesicles following dilution may range from one tenth of the concentration of the encapsulated IHP solution to a concentration equimolar therewith. For example, a 170 μg/ml. suspension of phosphatidylcholine, phosphatidylserine and cholesterol at a molar ratio of 8:2:7 may be sonicated for an hour and the resulting suspension of lipid vesicles frozen and diluted 1:1 with water after thawing and before use.

Prior to incubation with the IHP-containing lipid vesicles, erythrocytes are separated from the blood plasma and washed. The erythrocytes are mixed with the suspension of lipid vesicles and incubated at pH 7.0 to 8.0 at a temperature of 18° to 37° C. for from about ½ to 2 hours, preferably for 1 hour at 37° C. for human red cells. The erythrocytes, now modified by inclusion of IHP bound to the hemoglobin therein, are carefully washed to remove extracellular IHP, suspended in blood plasma or in any art-recognized blood plasma substitute, and transfused to a patient in need of increased oxygen supply to some tissues. The erythrocytes may be returned to the individual from whose blood they were isolated or may be administered to another individual of the same species and antigenic type, the donated erythrocytes being matched to the patient according to art-recognized blood typing procedures. The modified erythrocyte-containing blood or blood substitute may be transfused immediately to a patient in need thereof or may be stored under standard blood bank conditions until needed.

The present invention relates to a method for rendering lipid vesicle suspensions, such as the IHP-laden lipid vesicle suspensions described hereinabove, stable to long term storage at low temperature. This method is not limited to these IHP-containing lipid vesicle compositions, but may be applied to lipid vesicle suspensions without regard to the specific composition of the lipids, biologically active agent, and vehicle or to the method by which the suspension was prepared. Methods for the preparation of lipid vesicle suspensions encapsulating other agents are well known and are described, for example in "Annals of the New York Academy of Sciences, Volume 308 (D. Papahadjopoulos, Ed; N.Y. Acad. Sci., N.Y., 1978).

Membranes such as those of lipid vesicles are normally considered unstable to freezing temperatures. As the lipid membrane of the lipid vesicles is held together by ordinary intermolecular attractive forces, it is to be expected that freezing should cause the vesicles to burst, releasing the contents encapsulated therein. Surprisingly, it has been found that lipid vesicles, such as the IHP-containing lipid vesicles prepared by the foregoing method, are not fragmented by freezing at temperatures below −30° C. These lipid vesicles may be frozen without damage to the integrity of their lipid membranes and without leakage of their contents. The frozen liposomes have been found to be storage-stable at temperatures below the freezing temperature of the encapsulated solution from about −196° to −20° C. Whereas freshly prepared IHP-containing liposomes lose their capacity to transport IHP into erythrocytes in therapeutic amounts within 2 days, frozen liposomes remain intact and effective on thawing after having been frozen for months or, if stored in non-oxidizing atmosphere, years. The freezing and thawing of the lipid vesicles does not require complex specialized equipment. The suspension may be frozen simply by placement in a mechanical refrigerator at a temperature of −30° C. or less or by immersion in a non aqueous cooling bath at a temperature of from about −196° C. to about −30° C. The preferred method of freezing suspensions of lipid vesicles encapsulating a biologically active substance, such as IHP, is by immersion in a cold-stable container of such a lipid vesicle suspension in liquid propane at a temperature of from about −190° C. to about −141° C. The most preferred method is to freeze the lipid vesicle suspension at a temperature between about −189° C. and −170° C., in propane at a temperature close to its freezing point, −190° C., but far below its boiling point, −141° C., at which the propane remains in the liquid state. The freezing of lipid vesicle suspensions in a liquid propane bath has been found to be nearly instantaneous, requiring only a few minutes for full freezing.

Other non-aqueous cooling baths suitable freezing lipid vesicle suspensions include other liquified gases, for example air, nitrogen, oxygen or ammonia, and mixtures of solid carbon dioxide with organic compounds, such as alcohol, ether, or chloroform. The freezing time in liquid propane is shorter than, for example, in liquid nitrogen. During this rapid freezing procedure lipid vesicles are stable with regard to their membrane structure.

No complex speciallized equipment is required for the rapid freezing of lipid vesicles laden with biologically active agents. For example, when a polyethylene vial of an IHP-laden lipid vesicle suspension prepared as hereinabove described is placed in a polyethylene beaker of propane at −183° C., which is itself contained within a Dewar flask of liquid nitrogen, the lipid vesicle suspension is deep-frozen within about two minutes without damage to the membrane structure of the lipid vesicles and thus rendered stable to storage at a temperature of from −196° C. to −20° C.

Stored deep frozen lipid vesicle suspensions are readied for use by thawing at room temperature.

The additional steps of freezing and thawing the liposome suspension greatly improves the known method of decreasing the oxygen affinity of erythrocytes by modification of hemoglobin with IHP. The storage-stable liposomes may be prepared in large batches in a central location, realizing great savings in time, labor, and capital equipment. The lipid vesicles can be frozen in bulk or in small containers of a size suitable for the modification of a single unit of erythrocytes, and may be shipped in the frozen state to hospitals and blood banks. The frozen lipid vesicles may be stored until needed, thawed, and used in the same manner as freshly prepared lipid vesicles.

Similarly, lipid vesicle suspensions wherein the lipid vesicles are laden with other biologically active agents may be fast-frozen, stored at a temperature between about −196° C. and −20° C., and thawed before being used in the same manner as are fresh lipid vesicle suspensions of the same composition.

The following example illustrates the successful retention of IHP liposome activity after months of storage: Lipid vesicles composed of phosphatidylcholine, phosphatidylserine and cholesterol in a molar ratio of 8:2:7 with a total lipid concentration of 170 μg/ml including 0.19 M IHP and suspended in 0.19 M IHP buffered in 0.068 M bis-Tris pH 7.4 were frozen at −183° C. and thereafter stored at −30° C.

Figure 2:
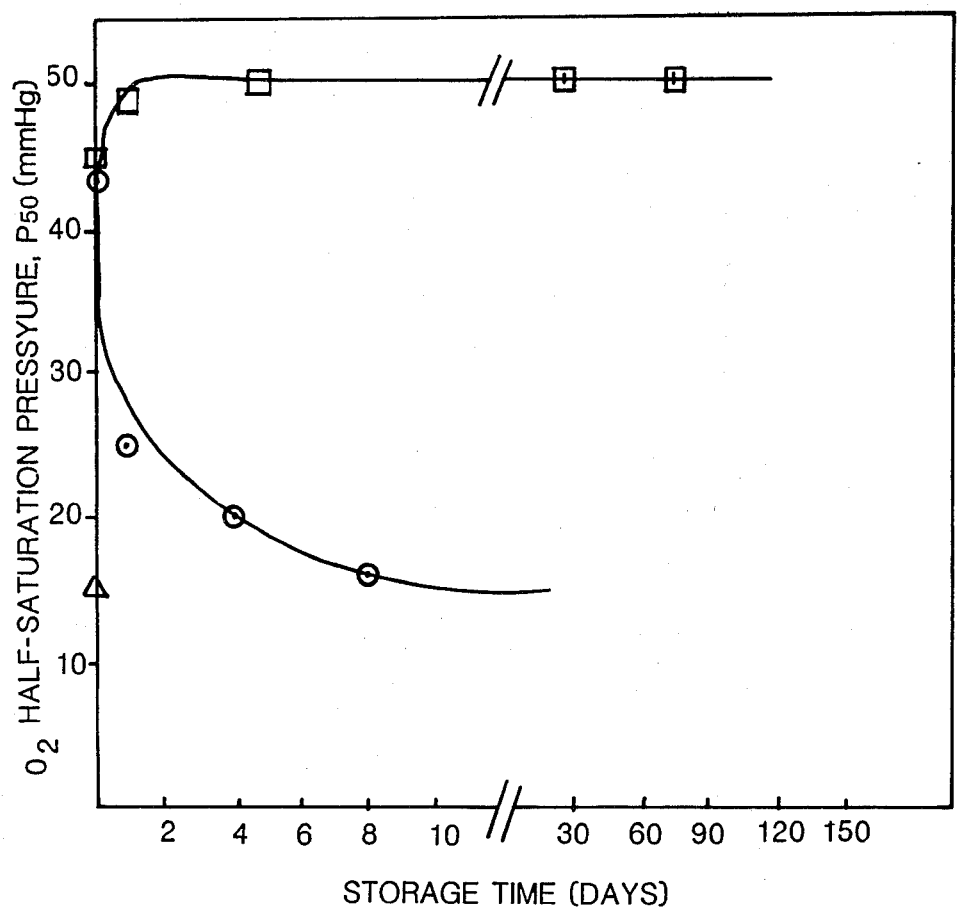
FIG. 2 is a graph showing IHP uptake by RBC measured as change in $p_{50}$ mediated by storage-stable (—□—□—□—), and storage-instable (—O—O—O—) V2 vesicles with 0.19 M IHP in the inside and in the outside medium respectively. Storage at 37° C. ( O O O ), at −30° C. after freezing at −183° C. ( □ □ □ ); fresh RBC before incubation with V2 vesicles.

The IHP uptake by RBC measured as change in $p_{50}$ mediated by storage-stable and storage-instable V2 vesicles have been shown in FIG. 2.

Samples of the frozen lipid vesicle suspension were thawed at room temperature after various periods of storage and incubated with human red blood cells and the oxygen half-saturation pressure, $p_{50}$, compared with that of red blood cells incubated with lipid vesicle a suspension of the same composition, which had been stored for the same period at 37° C.

Freshly prepared lipid vesicles changed the $p_{50}$ of human red blood cells from 15 mmHg to 44 mmHg. The 37° C.-stored vesicles have completely lost their ability to mediate IHP uptake by red blood cells after 8 days; the half-life time is about 1 day. Vesicles which were frozen at −183° C. and stored at −30° C., however, are characterized by a constant ability to mediate IHP uptake into red cells for a period of 2.5 months. FIG. 2 shows that the $p_{50}$ of red blood cells incubated with vesicles stored at low temperature and thawed remains constant and is slightly increased.

We claim:

1. The process for preparing an aqueous lipid vesicle suspension, wherein a biologically active agent is encapsulated within a unilamellar phopholipid membrane, stable to long term storage at temperatures of $-20°$ C. and below, which comprises rapidly freezing the lipid vesicle suspension at a temperature of from about $-196°$ C. to about $-30°$ C., wherein the lipid vesicle suspension is frozen in a liquid propane bath at a temperature of from $-190°$ C. to $-141°$ C.

2. The process according to claim 1 wherein the encapsulated biologically active agent is inositol hexaphosphate.

3. The process according to claim 1 wherein the phospholipid membrane comprises phosphatidylcholine, phosphatidylserine and cholesterol in a molar ratio of from 10 to 5:from 4 to 1:from 10 to 3.

4. The process of claim 3 wherein the membrane comprises phosphatidylcholine, phosphatidylserine and cholesterol in a ratio of 8:2:7.

5. A storage stable lipid vesicle suspension prepared according to claim 1 wherein the encapsulated biologically active agent is inositol hexaphosphate in an aqueous, buffered solution.

6. The storage stable lipid vesicle suspension of claim 5 wherein the phospholipid membrane comprises phosphatidylcholine, phosphatidylserine and cholesterol in a molar ratio of from 10 to 5:from 4 to 1:from 10 to 3.

7. The storage stable lipid vesicle suspension of claim 6 wherein the phospholipid membrane comprises phosphatidylcholine, phosphatidylserine and cholesterol in a ratio of 8:2:7.

8. In a process for preparing an aqueous lipid vesicle suspension, a biologically active agent being encapsulated in an aqueous buffered solution within a unilamellar phospholipid membrane in said suspension, and wherein said suspension has a predetermined freezing point, the steps comprising rapidly freezing the lipid vesicle suspension at a temperature of from about $-196°$ C. to about $-30°$ C. following preparation of said lipid vesicle suspension, subsequently storing said lipid vesicle suspension at a temperature below said freezing point so as to be stable for long term storage, and thereafter thawing said lipid vesicle suspension to a temperature suitable for said lipid vesicle suspension to be carried into living cells.

9. The process as claimed in claim 8 further comprising the step of ensonifying said liquid vesicle suspension at an energy of about 100 watts per square centimeter.

10. The process as claimed in claim 8, wherein said liquid vesicle suspension is stored at a temperature range from about $-20°$ C. to about $-30°$ C.

11. A storage stable lipid vesicle suspension prepared according to the process of claim 9, and wherein the biologically active agent includes inositol hexaphosphate.

12. A storage stable lipid vesicle suspension prepared according to the procedure of claim 1 or claim 9.

* * * * *